United States Patent [19]

Steckhan et al.

[11] Patent Number: 4,681,977

[45] Date of Patent: Jul. 21, 1987

[54] PREPARATION OF CHLORO-OLEFINS

[75] Inventors: Eberhard Steckhan, Meckenheim; Reinhard Wolf, Koenigswinter-Thomasberg; Hermann Puetter, Neustadt, all of Fed. Rep. of Germany

[73] Assignee: BASF Aktiengesellschaft, Ludwigshafen, Fed. Rep. of Germany

[21] Appl. No.: 749,423

[22] Filed: Jun. 27, 1985

[30] Foreign Application Priority Data

Jun. 28, 1984 [DE] Fed. Rep. of Germany ....... 3423762

[51] Int. Cl.$^4$ .............................. C07C 67/317
[52] U.S. Cl. ............................ 560/262; 562/598; 570/217; 568/315; 568/347; 568/392; 568/821; 568/850; 568/841
[58] Field of Search ............... 568/327, 315, 347, 392, 568/821, 850, 841; 570/217; 560/202; 562/598; 570/217

[56] References Cited

U.S. PATENT DOCUMENTS

| 4,018,838 | 4/1977 | Cleare ............................... 570/217 |
| 4,053,380 | 10/1977 | Fujita et al. ....................... 570/217 |
| 4,078,008 | 3/1978 | Lantzsch et al. .................. 570/217 |
| 4,081,488 | 3/1978 | Scharpf .............................. 570/217 |
| 4,098,657 | 7/1978 | Kay et al. ........................... 570/217 |
| 4,335,253 | 6/1982 | Kramer .............................. 570/217 |
| 4,450,309 | 3/1984 | Soos et al. .......................... 570/217 |

FOREIGN PATENT DOCUMENTS 1804728  3/1972  Fed. Rep. of Germany ...... 568/392
151187   8/1981  German Democratic Rep. .................................. 570/217

OTHER PUBLICATIONS

Stepham et al., Tet Letters, vol. 25, pp. 5649–4652 (1984).
Willmann et al., Angeus Chem. Int. ed, vol. 19, pp. 46–47 (1980).
Fieser et al., "Reagents for Organic Synthesis", J. Wiley & Sons, pp. 149–151 (1967).

Primary Examiner—James H. Reamer
Attorney, Agent, or Firm—Oblon, Fisher, Spivak, McClelland & Maier

[57] ABSTRACT

Chloro-olefins which contain a group of the formula

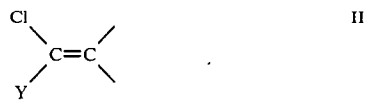

where Y is chlorine or hydrogen, which are prepared by a process in which a trichloromethyl compound which contains a group of the general formula

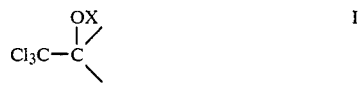

where X is hydrogen or an organic radical, is reduced with a chromium(II) salt in an aqueous medium.

5 Claims, No Drawings

/ 1

PREPARATION OF CHLORO-OLEFINS

FIELD OF THE INVENTION

The present invention relates to a process for the preparation of chloro-olefins by treating a trichloromethyl compound with a chromium(II) salt in an aqueous medium and to novel chloro-olefins.

DESCRIPTION OF THE RELATED ART

Chloro-olefins are desirable intermediate which are required, for example, for the preparation of pyrethroids.

They are obtained, for example, by reduction of 1,1,1-trichloromethyl-2-hydroxy compounds. In a process described in German Laid-Open Application DOS 2,657,148, halo alcohols of this type are dehydrochlorinated electrochemically to give the corresponding halogenated diene compounds. The halo alcohols can also be acetylated, and converted to the chloro-olefins by treatment with zinc dust (Coll. Czech. Chem. Commun. 1959, 24, 2230–2236). Another electrochemical process, in which β-trihalomethyl-β-propiolactones are reduced cathodically to dihalovinylacetic acids, is disclosed in East German Pat. No. 151,187.

These processes have various disadvantages. The reduction with zinc inevitably produces zinc salts, which pollute the environment. Moreover, the starting material must generally first be acetylated in an additional process step. Although the electrochemical reduction is more advantageous, it suffers, like all conventional processes involving direct electrochemical reduction, from the disadvantage that the reaction has to be carried out in homogeneous solution. It is therefore necessary to use solvents such as acetic acid. Since it is impossible to avoid the use of relatively large amounts of organic solvents in the anode space too, losses cannot be prevented. This also results in a reduction in the life of the anodes due to corrosion. Finally, it is difficult to go beyond the stage of the dichloro compound in the electrochemical reduction of trichloromethyl compounds. In general, monochloro-olefins are not formed.

SUMMARY OF THE INVENTION

We have found that trichloromethyl compounds which contain a group of the general formula

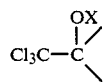   I where X is hydrogen or an organic radical, can be reduced to chloro-olefins which contain a group of the formula

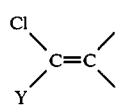   II where Y is chlorine or hydrogen, in a substantially more advantageous manner if the reduction is carried out in an aqueous medium using a chromium(II) salt.

DESCRIPTION OF THE PREFERRED EMBODIMENTS

Using the novel process, for example, chloro-olefins of the formula

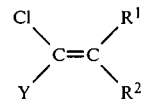   III where Y is chlorine or hydrogen, $R^1$ is hydrogen, a hydrocarbon radical or a radical which, together with $R^2$, is a member of a hydrocarbon ring, $R^2$ is a carboxyl, carbalkoxy, carboxamide, nitrile or acyl group, a hydrocarbon radical which may contain halogen atoms or hydroxyl, keto, carboxyl, carbalkoxy, carboxamide, nitrile or acyl groups, or a radical which, together with $R^1$, is a member of a hydrocarbon ring, can be prepared by reducing a trichloromethyl compound of the formula

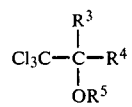   IV where $R^3$ is hydrogen, a hydrocarbon radical or a radical which, together with $R^4$, is a member of a hydrocarbon ring, $R^4$ is a carboxyl, carbalkoxy, carboxamide, nitrile or acyl group, a hydrocarbon radical which may contain halogen atoms or hydroxyl, keto, carboxyl, carbalkoxy, carboxamide, nitrile or acyl groups, or a radical which, together with $R^3$, is a member of a hydrocarbon ring, or a radical which, together with $-OR^5$, is a member of a cyclic ether or of a lactone ring, $R^5$ is hydrogen, alkyl, acyl or a radical which, together with $R^4$, is a member of a cyclic ether or of a lactone ring.

In the trichloromethyl compounds of the formula IV which are used as starting compounds, the hydrocarbon radical $R^3$ is, for example, alkyl, cycloalkyl, alkenyl, alkynyl or benzyl, preferably alkyl of 1 to 3 carbon atoms. Examples of hydrocarbon rings of which $R^3$ and $R^4$ are members are cycloaliphatic $C_4$–$C_8$-rings. The hydrocarbon radical $R^4$ is of, for example, 1 to 12 carbon atoms, and may be substituted by halogen atoms or hydroxyl, keto, carbalkoxy, carboxamide, nitrile or acyl groups. Examples of hydrocarbon radicals of this type are alkyl, cycloalkyl, alkenyl, alkynyl, aryl and benzyl.

Examples of cyclic ethers or lactone rings of which $-OR^5$ and $R^4$ are members are saturated or unsaturated 4-membered to 10-membered, preferably 4-membered to 6-membered, rings.

The trichloromethyl compounds used as starting materials can be obtained by conventional methods, for example acid-catalyzed addition reactions of chloral with olefins, aldol reactions of chloral with carbonyl compounds, or addition reactions of trichloromethyl anions with carbonyl compounds.

In the chloro-olefins of the general formula III which are obtainable by the novel process, in the majority of cases $R^1$ and $R^2$ are identical to the radicals $R^3$ and $R^4$ in the starting compounds of the formula IV. However, $R^1$ and $R^2$ may also differ from $R^3$ and $R^4$. Thus, a chloro-olefin of the formula III, where $R^1$ is hydrogen and $R^2$ is a carboxamide group, is obtained from, for example, the starting compound of the formula IV where $R^3$ and $R^5$ are each hydrogen and $R^4$ is a nitrile group.

The present invention furthermore relates to the novel chloro-olefins of the general formula

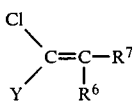

where Y is chlorine or hydrogen, $R^6$ is hydrogen or methyl, $R^7$ is one of the radicals

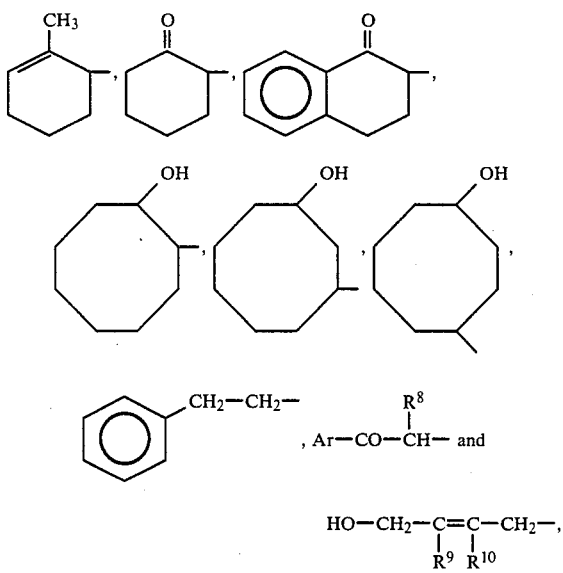

Ar is aryl, $R^8$ is methyl, hydrogen, chlorine or bromine, and $R^9$ and $R^{10}$ are each hydrogen or methyl.

These novel chloro-olefins can be used as, for example, intermediates for the preparations of drugs and crop protection agents.

In the novel process, the starting compounds in an aqueous medium are treated with the chromium(II) salts. Particularly suitable salts are chromium(II) salts of mineral acids or carboxylic acids, in particular the chlorides, sulfates and acetates, preferably the chlorides or acetates. The chromium is present in these salts in general in the form of a complex which possesses, for example, aquo or amino ligands. The chromium salts are preferably employed in aqueous solution, which should have a pH of <5, in particular ≦3.5, in order to suppress hydrolysis of the chromium salts. Advantageously, from 2 to 6 moles of the chromium(II) salt are used per mole of the trichloromethyl compound.

The trichloromethyl compound is treated with the chromium(II) salt at from −35° to 110° C., preferably from 0° to 50° C., and under from 0 to 20, preferably from 0.7 to 2, bar. The content of $Cr^{2+}$ in the aqueous reaction mixture is, for example, from 3 to 0.001 mole/kg, the initial concentration of $Cr^{2+}$ advantageously being from 0.01 to 2 moles/kg. The reaction medium can be completely aqueous or may consist of a mixture of water with an organic solvent, the content of solvents being not more than 70% by weight, preferably not more than 50% by weight. Particularly suitable solvents are water-miscible organic solvents, such as dimethylformamide, tetrahydrofuran, acetonitrile or dioxane. However, it is also possible to use a two-phase mixture containing a water-immiscible solvent, such as toluene, diethyl ether or methylene chloride.

In a particularly advantageous embodiment of the process of the invention, a solution of chromium(II) salts which has been prepared by electrochemical reduction of an aqueous solution of a chromium(III) salt is used.

In this procedure, the aqueous chromium(II) salt solution obtained by electrolysis is removed from the electrolysis cell and then used for the reduction of the trichloromethyl compounds (ex cell procedure). However, the reduction according to the invention may also be carried out simultaneously, i.e. during the electrolysis in the cathode space of the electrolysis cell (in cell procedure), the chromium salts being regenerated continuously.

The electrolysis is carried out using, for example, conventional partitioned cells, in particular plate cells and frame plate cells partitioned by ion exchange membranes. The cathode materials used are the conventional materials, such as mercury or another metal having a moderate to high hydrogen overvoltage, in particular lead, tin or zinc. Graphite or coated graphite grades as described in German Laid-Open Application DOS 3,300,865 are also suitable. In the in cell procedure, electrolysis is carried out, for example, at from 0° to 80° C. and at a current density of from 0.1 to 30 A/dm². The anolyte used is, for example, dilute sulfuric acid or hydrochloric acid, and may also contain the abovementioned chromium salts. Regeneration of the chromium salts after they have been used in the reduction according to the invention by the ex cell procedure can also advantageously be carried out by electrolysis.

In the novel process, the trichloromethyl compounds can be reduced to the corresponding chloro-olefins in a particularly advantageous manner. The fact that this reduction takes place so smoothly in an aqueous medium is surprising since previous attempts to reduce α-halo alcohols with chromium(II) salts (cf. Wellmann, doctoral thesis Indirekte elektrochemische Reduktionen organischer Verbindungen mit anorganischen Elektronenüberträgern (Indirect electrochemical reduction of organic compounds with inorganic electron carriers), Münster, 1979) gave positive results only in organic solvents and when water was substantially absent, and in particular only in the case of the more highly activated bromine compounds.

Because of the surprising finding that the process of this invention can be carried out so smoothly in an aqueous medium, the considerable economical advantages of combining the process with a procedure for regenerating the chromium salts can be utilized industrially. The anolyte used can be a purely aqueous solution. Since a predominantly aqueous phase is also used for the catholyte, there is little contamination of the anolyte by the catholyte. As shown in the comparative experiment without chromium salts (cf. Example 23), the direct electrochemical reduction of trichloromethyl compounds in an aqueous medium gives poor results, even after the addition of solubilizers.

EXAMPLES 1 TO 13

1 Part by volume of a 2 molar aqueous solution of $CrCl_2$ was mixed with 1 part by volume of dimethylformamide in the absence of oxygen at 0° C. The trichloromethyl compound shown in the Table was introduced into this mixture, while stirring, in an amount such that the $CrCl_2$ was present in a 4.2-fold molar excess. The pH of the solution was 3.5. The reaction mixture was then stirred for from 2 to 16 hours at room temperature, the reaction being monitored by gas chromatography or thin layer chromatography. The reaction mixture was worked up by adding from 3 to 6 times the volume of water, extracting several times with pentane, washing the solution and drying it, and distilling off the solvent. The crude chloroolefin compound obtained as the residue was purified by fractional distillation or by dissolving it in methylene chloride or in a mixture of methylene chloride with cyclohexane in a ratio of up to 1:1 and subjecting the solution to chromatography.

The CrCl$_2$ used was prepared in a conventional manner by treating CrCl$_3$ with zinc or by electrochemical reduction according to Example 22, paragraph c.

| Example | Trichloromethyl compound | Chloro-olefin and yield in % by weight | Duration of reaction [h] | Stereochemistry of the double bond (according to NMR) |
|---|---|---|---|---|
| 1 | cyclohexane-HO,CCl$_3$ | Cl,Cl-cyclohexylidene 63% ; H,Cl-cyclohexylidene 11% | 2 | — |
| 2 | cyclopentane-HO,CCl$_3$ | Cl,Cl-cyclopentylidene 40% ; H,Cl-cyclopentylidene 23% | 15 | — |
| 3 | H$_3$C,H$_3$C-C=C-CH$_2$-O-CH(CCl$_3$) | HO—CH$_2$—C(CH$_3$)=C(CH$_3$)—CH$_2$—CH=CHCl 66% | 3 | both cis |
| 4 | PhC(O)CH(CH$_3$)CH(OH)CCl$_3$ | PhC(O)CH(CH$_3$)CH=CHCl 62% | 2 | cis |
| 5 | cyclooctane fused oxetane with CCl$_3$ | cyclooctane-OH,CH=CHCl 71% ; cyclooctane-OH,CH=CCl$_2$ 13% | 4 | cis |
| 6 | H$_3$C-cyclohexenyl-CH(OH)CCl$_3$ | CH$_3$-cyclohexenyl-CH=CHCl 36% | 4 | cis |
| 7 | Ph-CH(OH)CCl$_3$ | Ph-CH=CHCl 44% ; Ph-CCl=CHCl 10% | 3 | cis |

| Example | Trichloromethyl compound | Chloro-olefin and yield in % by weight | Duration of reaction [h] | Stereochemistry of the double bond (according to NMR) |
|---|---|---|---|---|
| 8 | Ph-CH₂CH₂-C(OH)(CCl₃)(CH₃) | Ph-CH₂CH₂-C(CH₃)=CHCl 13%; Ph-CH₂CH₂-C(CH₃)=CCl₂ 56% | 16 | cis/trans mixture |
| 9 | CCl₃—CH(OH)—COOH | ClCH=CH—COOH (trans) 30% | 5 | trans |
| 10 | CCl₃-substituted β-lactone | Cl₂C=CH—COOH 80% | 5 | — |
| 11 | 2-(hydroxy-trichloromethyl-methyl)cyclohexanone | 2-(CH=CHCl)cyclohexanone 90% | 2 | preferably cis |
| 12 | CCl₃—CH(OAc)₂ | Cl—CH=CH—OAc 30%; Cl₂C=CH—OAc 1% | 16 | cis/trans 95:5 |
| 13 | H₂C=C(CH₃)—CH₂—CH(OH)—CCl₃ | H₂C=C(CH₃)—CH₂—CH=CHCl 60% | 6 | cis |

EXAMPLES 14 AND 15

Examples 4 and 5 were repeated using a water/dimethylformamide (DMF) mixture containing the substances in a different ratio.

| Example | Trichloromethyl compound | H₂O/DMF weight ratio | Chloro-olefin and yield in % by weight |
|---|---|---|---|
| 14 | cf. Example 4 | 75/25 | Ph-CO-CH(CH₃)-CH₂Cl 60% |
| 15 | cf. Example 5 | 85/15 | cycloheptanol-CH=CH—Cl 13%; cycloheptanol-CH=CCl₂ 64% |

EXAMPLE 16

(a) Preparation of the trichloromethyl compound 44.10 g (0.4 mole) of cyclooctene and 58.95 g (0.4 mole) of chloral in 60 ml of petroleum ether were initially taken in a 2-necked flask equipped with a magnetic stirrer, an internal thermometer and a drying tube. The mixture was cooled to ≦0° C. by means of a cold bath. 5.5 g (0.04 mole) of aluminum trichloride were added a little at a time in the course of 15 minutes, the temperature being kept at 0° C. Stirring was continued for a further 4 hours at this temperature, after which the mixture was left to stand for 15 hours at room temperature. For hydrolysis, the mixture was cooled to 0° C., and an equal volume of ice water was slowly added. The dark brown petroleum ether phase was separated off, filtered to remove the insoluble polymers and washed three times with saturated aqueous sodium chloride solution. The organic phase was dried over magnesium sulfate and evaporated down in a rotary evaporator. The crude product was purified by fractional distillation under reduced pressure (105°–118° C.; 0.5 mm Hg). 78 g (0.3 mole; 75% by weight) of a mixture of two compounds in a ratio of 1:1 were obtained. The two compounds were separated by liquid chromatography over a silica gel column (diameter 5 cm, length 20 cm) using a 1:1 cyclohexane/methylene chloride mixture as the mobile phase. In addition to 3-(1'-hydroxy-2',2',2'-trichloroethyl)-1-cyclooctene, a compound of the probable structure 8-trichloromethyl-7-oxabicyclo[4.2.2]decane, of the formula

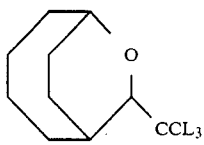

was isolated.

(b) Preparation of the chloro-olefin compound 9 ml of dimethylformamide were initially taken in a stirred flask and freed from oxygen by means of a stream of argon. 9.0 ml of an aqueous 1.48 molar (13.4 millimoles) Cr(II) chloride solution at pH 3.5 were then slowly added, while cooling with an ice bath. Thereafter, 0.86 g (3.3 millimoles) of the trichloromethyl compound having the probable structure given above, dissolved in a little dimethylformamide, was added. The ice bath was removed and the mixture was stirred for a further 5 hours. The solution was worked up by adding 4 times the volume of water and extracting the mixture with pentane. The organic phase was washed, and dried over magnesium sulfate, and the solvent was removed by distillation. Gas chromatography over a UV 101 column gave two intensive peaks for the product (relative peak area 65%) and for the unconverted educt (relative peak area 15%). The crude product (0.78 g) was separated over a silica gel column, using methylene chloride as the mobile phase. 0.42 g (67% yield; 71% conversion) of the product having the probable structure (Z)-4-(2'-chloroethen-1'-yl)-cyclooctan-1-ol, of the formula

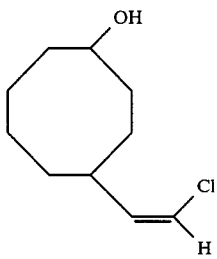

were obtained in this manner.

EXAMPLES 17 TO 21

The procedure described in Examples 1 to 13 were followed, except that neither dimethylformamide nor any other organic solvent was used. The pH of the solutions was 3.5 in Examples 17 and 18, while in Examples 19, 20 and 21 the solutions were brought to pH 1 by adding HCl.

| Example | Trichloromethyl compound | Chloro-olefin and yield in % by weight |
|---|---|---|
| 17 | OH<br>|<br>CCl$_3$—CH—COOH | Cl H<br>\\=/<br>H COOH<br>30% |
| 18 | H$_3$C OH<br>\\ |<br>H$_2$C—...—CCl$_3$ | H$_3$C Cl<br>\\ /<br>H$_2$C—...=...<br>55% |
| 19 | HO CCl$_3$<br>(cyclohexane) | Cl Cl / H Cl<br>(cyclohexylidene) (cyclohexylidene)<br>80% 14% |
| 20 | HO CCl$_3$<br>(cyclopentane) | Cl Cl / H Cl<br>(cyclopentylidene) (cyclopentylidene)<br>77% 8% |
| 21 | CH$_3$ OH<br>(cyclohexenyl)—CH—CCl$_3$ | CH$_3$<br>(cyclohexenyl)—CH=CH—Cl<br>8% |

EXAMPLE 22

Combination of the reduction according to the invention with the electrolytic recovery of CrCl$_2$.

(a) Electrolysis

The electrolysis was carried out in a partitioned cell which contained a Pb/PbO$_2$ anode and a Pb cathode, each having a surface area of 1 dm$^2$. The anode space and the cathode space were separated from one another by means of a $^R$NAFION cation exchange membrane. 1 kg of 5% strength sulfuric acid was used as the anolyte, while the catholyte employed was a solution of 106.5 g of CrCl$_3$. 6H$_2$O in 750 ml of water.

(b) In cell reduction

A solution of 18.9 g (0.1 mole) of 3-trichloromethyl-propiolactone in 500 ml of tetrahydrofuran was added to the catholyte, and electrolysis was carried out for 3 hours at room temperature and with a current of 5 A. Thereafter, the catholyte was extracted with methylene chloride, and the organic phase was dried and evaporated down in a rotary evaporator to give 13.2 g of 4,4-dichloro-3-butenoic acid (pure according to NMR spectroscopy). Yield: 85% by weight.

(c) Ex cell reduction

First, the CrCl$_3$ solution described in paragraph (a) was subjected to electrolysis according to paragraph (b), using a current of 5 A. The CrCl$_2$ solution obtained in this manner was added to a solution of 18.9 g (0.1 mole) of 3-trichloromethylpropiolactone in 500 ml of tetrahydrofuran, and the mixture was stirred for 2 hours at room temperature. The reaction mixture was worked up as described in paragraph (b) to give 11.9 g of 4,4-dichloro-3-butenoic acid (pure according to NMR spectroscopy). Yield: 77% by weight.

(d) Reuse of the chromium salt solution from (c)

The aqueous chromium salt solution recovered in the ex cell reduction according to paragraph (c) was reused for electrolysis by the method described in paragraph (c). In the subsequent reaction with 3-trichloromethyl-propiolactone, the procedure described in paragraph (c) was followed, except that 300 ml of dimethylformamide were used instead of 500 ml of tetrahydrofuran. 20.2 g of crude product were obtained. This product contained about 15 g of 4,4-dichloro-3-butenoic acid, the remainder being dimethylformamide. Yield: about 97% by weight. After distillation (bp. 95° C./2), analysis of the resulting product gave the following values:

found: C 31.6%, H 2.9%, O 20.9%, Cl 45.4%; calculated: C 30.9%, H 2.6%, O 20.7%, Cl 45.8%.

(e) In cell reduction with reuse of the electrolyte

A solution of 189.5 g (1 mole) of 3-trichloromethyl-propiolactone in 500 ml of tetrahydrofuran (THF) was added to the catholyte, and electrolysis was carried out for 7.75 hours at 50° C., using a current of 8 A (current used 62 Ah=116% of theory). The catholyte was then freed from the desired product by extracting with three times 200 ml of methylene chloride, mixed with fresh 3-trichloromethylpropiolactone in tetrahydrofuran and then fed to the electrolysis. This procedure was repeated three times.

The organic phase was washed with a little water, dried and evaporated down in a rotary evaporator. The yield of crude product was >95%. To obtain the desired product in pure form, the crude product (150.3 g (97%) of a yellow oil) was stirred with 300 g of water for half an hour, the resulting crystal slurry was cooled and filtered off under suction, and the precipitate was dried to give 129.3 g (84%) of 4,4-dichloro-3-butenoic acid in the form of white crystals of melting point 42° C.

EXAMPLE 23

(Comparative Experiment)

The electrolysis described in Example 18, paragraph (b), was repeated, but, instead of the chromium salt solution, a 5% strength by weight aqueous sodium chloride solution was used as the catholyte. Working up gave 18.2 g of a mixture which consisted of about 50% by weight of the starting compound, about 40% by weight of 4,4,4-trichloro-3-hydroxybutanoic acid and about 10% by weight of 4,4-dichloro-3-butenoic acid.

We claim:

1. A process for the preparation of a chloroolefin of the formula:

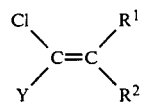

where Y is chlorine or hydrogen, $R^1$ is hydrogen, alkyl of 1 to 3 carbon atoms or a radical which, together with $R^2$ forms a cycloaliphatic $C_4$- to $C_8$-ring, $R^2$ is a carboxyl, carbalkoxy or a hydrocarbon radical which contains 1 to 12 carbon atoms and which may contain halogen atoms or hydroxyl or keto groups, or a radical which, together with $R^1$ forms a cycloaliphatic $C_4$- to $C_8$-ring, wherein a trichloromethyl compound of the formula

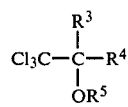

where $R^3$ is hydrogen, alkyl of 1 to 3 carbon atoms or a radical which, together with $R^4$ forms a cycloaliphatic $C_4$- to $C_8$-ring, $R^4$ is a carboxyl, carbalkoxy, or a hydrocarbon radical which contains 1 to 12 carbon atoms and which may contain halogen atoms or hydroxyl or keto groups, or a radical which, together with $R^3$ forms a cycloaliphatic $C_4$-$C_8$-ring or a radical which, together with —$OR^5$ forms a 4- to 6-membered cyclic ether or a lactone ring, and $R^5$ is hydrogen, alkyl, acyl or a radical, which, together with $R^4$ forms a 4- to 6-membered cyclic ether or a lactone ring, is treated with a chromium(II) salt in an aqueous medium at from −35° to 110° C.

2. The process of claim 1, wherein said chromium (II) salt is a salt of a mineral acid or a carboxylic acid.

3. The process of claim 2, wherein said chromium (II) salt is a chloride, sulfate or acetate.

4. A process as claimed in claim 1, wherein the solution of the chromium(II) salt used has been prepared by electrochemical reduction of an aqueous solution of a chromium(III) salt.

5. A process as claimed in claim 4, wherein the treatment of the trichloromethyl compound with the chromium(II) salt is carried out together with the electrochemical reduction of the chromium(III) salt in the cathode space of an electrolysis cell.

* * * * *